United States Patent [19]

Smith

[11] Patent Number: 4,888,447
[45] Date of Patent: Dec. 19, 1989

[54] PROCESS FOR PREPARING ALKOXYLATED TERTIARY AMINES

[75] Inventor: Kim R. Smith, Baton Rouge, La.

[73] Assignee: Ethyl Corporation, Richmond, Va.

[21] Appl. No.: 213,346

[22] Filed: Jun. 30, 1988

[51] Int. Cl.$^4$ .................. C07C 85/06; C07C 87/62; C07C 93/06; C07C 87/28

[52] U.S. Cl. .................. 564/480; 564/305; 564/336; 564/346; 564/353; 564/354; 564/349; 564/401; 564/402; 564/474

[58] Field of Search .............. 564/305, 336, 353, 346, 564/354, 399, 401, 402, 474, 480

[56] References Cited

U.S. PATENT DOCUMENTS

| | | | |
|---|---|---|---|
| 3,347,921 | 10/1967 | Carrubba et al. | 260/581 |
| 3,442,950 | 5/1969 | Barker | 260/576 |
| 4,181,682 | 1/1980 | Watts, Jr. et al. | 260/584 B |
| 4,495,369 | 1/1985 | Werner et al. | 564/480 |

FOREIGN PATENT DOCUMENTS 0180455  5/1986  European Pat. Off. .

*Primary Examiner*—Richard L. Raymond
*Assistant Examiner*—Peter G. O'Sullivan

[57] ABSTRACT

A process is described for selectively preparing alkoxylated tertiary amine compounds, such as aminated ethoxylated amines, at ambient pressure by reacting an oxyalkylated alcohol with a secondary amine in the presence of a reductive amination catalyst at above ambient temperature using, as a reductive amination catalyst, a combination of Raney nickel and molybdenum.

14 Claims, No Drawings

PROCESS FOR PREPARING ALKOXYLATED TERTIARY AMINES

BACKGROUND OF THE INVENTION

This invention relates to the preparation of alkoxylated tertiary amines and, more particularly, to an improved process for the preparation of alkoxylated tertiary amines from an oxyalkylated alcohol and a secondary amine using, as an amination catalyst, a catalyst obtained by combining Raney nickel and molybdenum. The alkoxylated tertiary amines made by the process of the invention are useful as biocides, corrosion inhibitors and fuel additives.

It is known in the art to manufacture alkoxylated tertiary amine compounds by reacting an oxyalkylated alcohol with a secondary amine in the presence of a reductive amination catalyst.

Kesling et al., European Patent Application No. 0 180 455 discloses a process for selectively preparing alkoxylated tertiary amine compounds having the general formula:

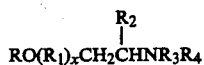

by reacting an oxyalkylated alcohol of the formula:

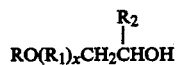

or a mixture of such alcohols, with a secondary amine of the formula $HNR_3R_4$ at a temperature in the range of from about 150° C. to 325° C. and a pressure of from about 50 psig to 3000 psig in the presence of from 0.5 to 20 wt % of an amination catalyst based on the total reaction mixture and wherein R is a straight or branched chain alkyl group having from 1 to 11 carbon atoms, a cyclic alkyl group having from 5 to 10 carbon atoms, an aryl group having up to 12 carbon atoms, or an aralkyl or alkaryl group having up to 18 carbon atoms, $R_1$ is a single unit or a series of units of the formula:

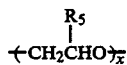

wherein in each unit $R_5$ is independently selected from the group consisting of hydrogen and a straight or branched chain alkyl group having from 1 to 12 carbon atoms and x is an integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

Amination catalysts described as being useful in the proess include Raney nickel, supported noble metals, and catalysts containing Cu, Cr and promoters such as nickel. Catalysts containing CuO and $Cr_2O_3$ in various ratios, Cu-Cr supported on magnesium aluminate spinel and ruthenium on activated carbon are reported to be preferred catalysts. A selectivity to the alkoxylated tertiary amine product of 98% using, as an amination catalyst, 5 wt % copper chromite supported on magnesium aluminate spinel is disclosed in Example 31.

One disadvantage of this process is that it is carried out at elevated pressures of from about 50 psig to 3000 psig, preferably from about 100 psig to 250 psig which necessitates the use of pressure equipment. Accordingly, it would be advantageous if the process could be conducted at ambient pressure so that the use of such equipment could be avoided.

SUMMARY OF THE INVENTION

It has now been discovered that alkoxylated tertiary amine compounds of the type generally described in Kesling et al., European Patent Application No. 0 180 455 can be produced in high selectivities at ambient pressure by conducting the amination reaction described therein using, as an amination catalyst, a molybdenum-promoted Raney nickel catalyst. Selectivity to the alkoxylated tertiary amine of up to 99% based on the total nitrogen content of the reaction product has been obtained by the process of the present invention employing such a catalyst.

DESCRIPTION OF THE PREFERRED EMBODIMENT

Thus, the present invention is embodied in a method for selectively preparing at ambient pressure an alkoxylated tertiary amine compound having the formula:

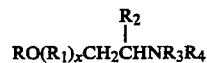

or a mixture of such amines by reacting an oxyalkylated alcohol of the formula:

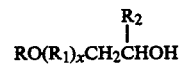

or a mixture of such alcohols, with a secondary amine of the formula $HNR_3R_4$ at elevated temperature in the presence of a catalytic quantity of an amination catalyst consisting of a combination of Raney nickel and molybdenum wherein R is a straight or branched chain alkyl group having from 1 to 20 carbon atoms, a cyclic alkyl group having from 5 to !0 carbon atoms, an aryl group having up to 12 carbon atoms, or an aralkyl or alkaryl group having up to 18 carbon atoms, R is a single gunit or a series of units of the formula:

wherein in each unit $R_5$ is independently selected from the group consisting of hydrogen and a straight or branched chain alkyl group having from 1 to 12 carbon atoms and x is an integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

The process of this invention is employed in the conversion of oxyalkylated alcohols to alkoxylated tertiary amines in high selectivities at ambient pressure.

The alkoxylated tertiary amine compounds are prepared by reacting an alcohol or mixtures of alcohols with an alkylene oxide to prepare an oxyalkylated alcohol followed by the catalytic amination of the oxyalkylated alcohol with a secondary amine such as a dialkyl, dicyclic alkyl, dibenzyl or diallyl amine at ambient pressure using, as an amination catalyst, a combination of Raney nickel and molybdenum.

The oxyalkylation reaction is conducted by methods well-known in the art by reacting an appropriate alcohol, such as methanol, etc. or $C_6$ through $C_{20}$ linear primary alcohols or linear primary alcohols containing various mixtures of $C_6$ through $C_{20}$ alcohols with an alkylene oxide, such as ethylene oxide, in the presence of an alkali metal or alkaline earth metal catalyst. Typical of such alcohols, which are employed in the present invention, are the EPAL 610 ® linear primary alcohols or EPAL 810 ® linear primary alcohols which are mixtures of predominantly $C_8$ and $C_{10}$ straight chain alcohols and EPAL 1214 ® linear primary alcohols which are mixtures of predominantly $C_{12}$ and $C_{14}$ straight chain alcohols sold commercially by Ethyl Corporation.

The alcohols which may be reacted with the alkylene oxides to prepare the oxyalkylated alcohols for further processing include any aliphatic or branched monohydric alcohol containing from 1 to 20 carbon atoms, cyclic alcohols, aryl alcohols, as well as aralkyl and alkaryl alcohols as defined by R in the above formula. Specific examples include, for instance, methyl, ethyl, n-propyl, isopropyl, tert-butyl, hexyl, octyl, decyl, dodecyl, tetradecyl, benzyl alcohols, cyclohexanol, 3-methyl butanol, 1-heptanol and the like or mixtures thereof.

The alkylene oxides which may be employed to prepare the oxyalkylated alcohols include, for example, ethylene and propylene oxide and the higher alkylene oxides, i.e. containing from 3 to 12 carbon atoms as taught in Kesling et al., European Patent Application No. 0 180 455 incorporated herein by reference. A preferred alkylene oxide is ethylene oxide.

In general, the oxyalkylated alcohol formation is carried ut at temperatures ranging from about 70° C. to 150° C. under moderately elevated pressures in the presence of an alkaline-reacting material or catalyst such as sodium, potassium and calcium.

Several oxyalkylated alcohols are commercially available such as Ethonic TM 1214-2 alcohol ethoxylate, an alcohol ethoxylate derived from a mixture of predominantly $C_{12}$ and $C_{14}$ linear primary alcohols having an approximate degree of ethoxylation of 2, Ethonic TM 1214-3 alcohol ethoxylate, an alcohol ethoxylate derived from a mixture of predominantly $C_{12}$ and $C_{14}$ linear primary alcohols having an approximate degree of ethoxylation of 3, and Ethonic TM 1214-6.5 alcohol ethoxylate, an alcohol ethoxylate derived from a mixture of predominantly $C_{12}$ and $C_{14}$ linear primary alcohols having an approximate degree of ethoxylation of 6.5, sold commercially by the Ethyl Corporation.

Preparation of the alkoxylated tertiary amine involves the process of aminating the oxyalkylated alcohol with a secondary amine in the presence of a catalytic quantity of an amination catalyst obtained by combining Raney nickel and molybdenum.

Specific examples of secondary amines which may be used to aminate the oxyalkylated alcohols include, for example, dimethylamine, diethylamine, di-n-butylamine, di-n-decylamine, di-benzylamine, dicyclohexylamine, and diallylamine.

In general, the reaction is conducted at elevated temperature at ambient pressure in the presence of a catalytic quantity of a molybdenum-promoted Raney nickel catalyst for a period of time sufficient for the nitrogen content of the reaction mixture to reach an equilibrium level. The reaction is carried out in the presence of hydrogen.

The reaction can be conducted batchwise by merely placing the molybdenum-promoted Raney nickel catalyst in the oxyalkylated alcohol and feeding secondary amine while stirring at reaction temperature. Alternatively, the reaction can be conducted continuously as, for example, by placing the catalyst in a packed or fluidized bed through which the oxyalkylated alcohol is circulated and secondary amine added at reaction temperatures.

The reaction is conducted at a temperature high enough to cause the reaction to proceed at a reasonable rate but not so high as to cause decomposition of the reactants or products. A useful range is from about 150° C. to 350° C., preferably from about 175° C. to 275° C.

The reaction should be conducted for a time sufficient to achieve the desired degree of completion of the reaction. The reaction time is not a truly independent variable but is at least dependent to some extent on the other process conditions employed. In general, higher temperatures should afford a faster reaction time while, on the other hand, lower reaction temperatures should tend to increase the time of reaction. Further, the reaction time will generally be dependent on the choice of oxyalkylated alcohols and secondary amine reactants used in the process, amount of catalyst, type of equipment used, and whether the process is continuous or batch. Good results are obtained in 1 to 8 hours with the more preferable range being from 2 to 6 hours.

The amount of catalyst employed in the process is a catalytic amount. By catalytic amount is meant an amount of catalyst sufficient to catalyze the conversion of oxyalkylated alcohol and secondary amine reactants to the corresponding alkoxylated tertiary amine compounds in high selectivities in a reasonable reaction time at ambient pressure. In general, from about 0.01 to about 50 wt % of a molybdenum-promoted Raney nickel catalyst based on the weight of the starting oxyalkylated alcohol reactant containing from about 0.1 to 50 wt % molybdenum based on the total weight of the catalyst is used. A preferred range is from about 0.5 to 15 wt %. Molybdenum-containing Raney nickel catalysts are available commercially. For example, a molybdenumpromoted Raney nickel catalyst containing 2.0 wt % molybdenum designated "Raney-30" is sold commercially by W. R. Grace & Co., P.O. Box 2117, Baltimore, Md., 21203. The catalyst is sold as a slurry in water consisting of approximately 50% solids and 50% water, by weight. This form minimizes problems stemming from the pyrophoric nature of the catalyst in the dry state.

The amount of secondary amine employed in the process should be at least a stoichiometric amount. This is 1.0 mol per mol of oxyalkylated alcohol. The secondary amine is preferably used in excess. A preferred amount is about 1.0 to 6.0 mol of secondary amine per mol of oxyalkylated alcohol reactant. A more preferred amount is about 1.0 to 4.0 mol of secondary amine per mol of oxyalkylated alcohol with a still more preferred amount being 1.0 to 2.0 mol of secondary amine per mol of oxyalkylated alcohol. The excess of secondary amine functions to insure maximum alkoxylated tertiary amine production.

The reaction mixture formed as a result of the reductive amination of the oxyalkylated alcohol may be recovered and fractionated in any suitable manner, such as by fractional distillation to obtain the desired alkoxylated tertiary amine product.

The following examples show how to conduct the process of the invention using a molybdenum-promoted Raney nickel catalyst and compare it to conducting the process using a non-molyb- denum-promoted Raney nickel catalyst.

EXAMPLE I

A 250-mL creased flask equipped with a mechanical stirrer (200 rpm), water condenser (20 C), thermocouple, gas sparge tube and water trap was charged with 3.5g of a molybdenum-promoted Raney nickel catalyst obtained from W. R. Grace & Co. identified as "Raney-30" and containing 2.0 wt % molybdenum and 100g (0.19 mol) of Ethonic ™ 1214-6.5 ethoxylated oligomer alcohol derived from a mixture of predominantly $C_{12}$ and $C_{14}$ linear primary alcohols having an approximate degree of ethoxylation of 6.5. The flask was swept with nitrogen for 15 minutes and the mixture was heated under hydrogen to 220° C. The reaction was carried out under a continuous hydrogen flow of 0.1 cf/hr. At 220° C. dimethylamine feed was initiated at a rate of 0.4 cf/hr (1.7 mol/hr). The reaction was stopped after 3 hours. The product was analyzed by $^{13}C$ NMR and titration methods to determine percent selectivity to the alkoxylated tertiary amine and by-product primary and secondary amines. Analysis indicated a selectivity to the alkoxylated tertiary amine of 99% based on the total nitrogen content of the reaction product. Analysis indicated no alkoxylated primary amine present in the reaction mixture product mixture and 1.0% of the alkoxylated secondary amine $(C_{12}-C_{14}-[EO]_{5.5}Et)_2NH$.

EXAMPLE II

Comparative Examole

This experiment was similar to Example I except that approximately 3.0 g of Raney nickel (no molybdenum promoter) was used as the amination catalyst in place of the "Raney 30" molybdenum-containing catalyst employed in Example I. Analysis after 4 hr indicated a selectivity to the alkoxylated tertiary amine of 66% based on the total nitrogen content of the reaction product. Other by-products were 31% alkoxylated secondary amine and 2.5% alkoxylated primary amine.

As the results show at ambient pressure, a selectivity to the alkoxylated tertiary amine of 99% was achieved using the molybdenum-promoted Raney nickel catalyst of the present invention compared to a selectivity to the alkoxylated tertiary amine of only 66% using a non-molybdenum-promoted Raney nickel catalyst.

EXAMPLE III

The batch reaction amination procedure of Example I was repeated using approximately 3.0 g of "Raney-30" catalyst and 105g (0.20 mol) of Ethonic ™ 1214-6.5 ethoxylated oligomer alcohol in the reaction. Analysis after 4 hr of reaction time indicated a 96% selectivity to the alkoxylated tertiary amine based on the total nitrogen content of the reaction product was obtained. Other by-products were 3.8% alkoxylated secondary amine and 0.0% alkoxylated primary amine.

What is claimed:

1. A process for selectively preparing at ambient pressure an alkoxylated tertiary amine having the formula:

or a mixture of such amines which comprises reacting an oxyalkylated alcohol of the formula:

or a mixture of such alcohols, with a secondary amine of the formula $HNR_3R_4$ at elevated temperature in the presence of a catalytic quantity of an amination catalyst consisting of a combination of Raney nickel and molybdenum wherein R is a straight or branched chain alkyl group having from 1 to 20 carbon atoms, a cyclic alkyl group having from 5 to 10 carbon atoms, an aryl hydrocarbon group having up to 12 carbon atoms, or an aralkyl or alkaryl hydrocarbon group having up to 18 carbon atoms, $R_1$ is a single unit or a series of units of the formula:

wherein in each unit $R_5$ is independently selected from the group consisting of hydrogen and a straight or branched chain alkyl group having from 1 to 12 carbon atoms and x is a integer of from 0 to 40, $R_2$ is hydrogen or a straight or branched chain alkyl group having from 1 to 12 carbon atoms, $R_3$ and $R_4$ are each independently selected from the group consisting of straight and branched chain alkyl groups having from 1 to 12 carbon atoms, cyclic alkyl groups having from 5 to 10 carbon atoms, 1 to 4 carbon atom alkyl substituted or unsubstituted benzyl groups and allyl.

2. A process according to claim 1 wherein R is a straight chain alkyl group having from 8 to 16 carbon atoms, $R_1$ is a

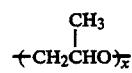

group with x being 7 and $R_2$, $R_3$ and $R_4$ are methyl groups.

3. A process according to claim 2 wherein $R_1$ is a

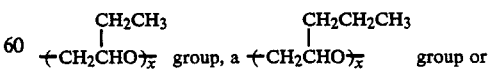

group or a

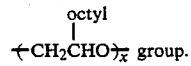

4. A process according to claim 1 wherein the process is conducted at a temperature in the range of from about 150° C. to about 350° C.

5. A process according to claim 1 wherein the amination catalyst is employed in an amount of from about 0.01 to about 50 wt % based on the weight of said oxyalkylated alcohol.

6. A process according to claim 1 wherein the amination catalyst contains from about 0.1 to about 50 wt % molybdenum based on the total weight of the catalyst.

7. In a process of producing alkoxylated tertiary amines by reacting an alkoxylated alcohol with a secondary amine, the improvement which comprises conducting the reaction at ambient pressure in the presence of a molybdenum-containing Raney nickel catalyst.

8. A process according to claim 7 wherein the alkoxylated alcohol is an ethoxylated primary alcohol in which the alkanol has up to 20 carbon atoms.

9. A process according to claim 7 wherein the alkoxylated alcohol is an ethoxylated alcohol in which the alkanol is predominantly a mixture of $C_{12}$ and $C_{14}$ linear alkanols.

10. A process according to claim 9 wherein the ethoxylated alkanol has an approximate degree of ethoxylation of 6.5.

11. A process according to claim 7 wherein the secondary amine is dimethylamine.

12. A process according to claim 11 wherein the alkoxylated alcohol is an ethoxylated primary alcohol in which the alkanol has up to 20 carbon atoms.

13. A process according to claim 11 wherein the alkoxylated alcohol is an ethoxylated alcohol in which the alkanol is predominantly a mixture of $C_{12}$ and $C_{14}$ linear alkanols.

14. A process according to claim 13 wherein the ethoxylated alkanol has an approximate degree of ethoxylation of 6.5.

* * * * *